(12) United States Patent
Wood et al.

(10) Patent No.: US 6,353,113 B1
(45) Date of Patent: Mar. 5, 2002

(54) PROCESS FOR THE PREPARATION OF 5-PERFLUOROALKYL SUBSTITUTED BENZOTRIAZOLE UV ABSORBERS

(75) Inventors: Mervin G. Wood, Poughquag; Deborah DeHessa, Poughkeepsie, both of NY (US); Andrew B. Naughton; Jerome Sanders, both of Mobile, AL (US); Jacqueline Lau, Jericho; Rong Xiong, Dobbs Ferry, both of NY (US); Joseph Babiarz, Amawalk, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/632,217

(22) Filed: Aug. 3, 2000

(51) Int. Cl.$^7$ .................... C07D 249/20; C07D 413/10; C07D 403/10; C07D 401/10
(52) U.S. Cl. ...................... 548/260; 546/199; 544/136; 544/366
(58) Field of Search ........................................ 548/260

(56) References Cited

U.S. PATENT DOCUMENTS 5,977,219 A    11/1999    Ravichandran et al. ....... 524/91

FOREIGN PATENT DOCUMENTS

| DE | 116230  | 11/1961 |
| GB | 2319035 | 5/1998  |
| JP | 357690  | 3/1991  |

*Primary Examiner*—Patricia L. Morris
(74) *Attorney, Agent, or Firm*—Luther A. R. Hall; Tyler A. Stevenson

(57) ABSTRACT

A process for preparing 2H-benzotriazole UV absorbers containing a perfluoroalkyl moiety at the 5-position of the benzo ring, preferably a trifluoromethyl group, involves diazotizing the perfluoroalkyl substituted o-nitroaniline using concentrated sulfuric acid plus sodium nitrite or preferably nitrosylsulfuric acid to form the corresponding monoazobenzene intermediate via the diazonium salt intermediate which is reduced to the corresponding 5-perfluoroalkyl substituted 2H-benzotriazole UV absorber compound by conventional reduction means.

28 Claims, No Drawings

PROCESS FOR THE PREPARATION OF 5-PERFLUOROALKYL SUBSTITUTED BENZOTRIAZOLE UV ABSORBERS

The instant invention pertains to a superior process for making 2H-benzotriazole UV absorbers which are substituted by a perfluoroalkyl group, i.e. trifluoromethyl, usually at the 5-position of the benzo ring.

BACKGROUND OF THE INVENTION

Japanese TOKU-KAI-Hei 3-57690 generically discloses compounds where the benzo ring of the benzotriazole may be substituted by a host of groups including hydrogen, alkyl, alkoxy, aryloxy, halogen, substituted amino, cyano, nitro, acyl and trihalomethyl. The only specific benzotriazole compounds mentioned are those where the benzo ring is unsubstituted or is substituted at the 5-position by a chloro group. There is no evidence that the Japanese inventors made any trihalomethyl substituted benzotriazole.

German Patent Application 116,230 describes inter alia the preparation of 5-trifluoromethyl-2-(2-hydroxy-5-methylphenyl)-2H-benzotriazolyl-1-oxide. The only synthesis conditions disclosed for the entire group of compounds prepared show the diazotization of the appropriate o-nitroaniline with aqueous sodium nitrite and hydrochloric acid. The German workers offer no synthetic details or more importantly no yield information for the preparation of 5-trifluoromethyl-2-(2-hydroxy-5-methylphenyl)-2H-benzotriazolyl-1-oxide.

In British Patent Application 2,319,035 and United States Pat. No. 5,977,219, all benzotriazole compounds containing a trifluoromethyl moiety at the 5-position of the benzo ring are referenced to the synthetic procedure of Example 1. Issues to be considered with this synthetic procedure are (a) a 100% excess of the diazonium salt relative to phenol is used; (b) the monoazo prepared by this method is described as a paste (generally materials with the consistency of a paste are impure); the pure monoazo is a solid with a melting point of 101–105° C.; (c) the yield of benzotriazole based on the phenol is 11% and is only 5.5% based on the $CF_3$-substituted o-nitroaniline; (d) the diazotization preparation in Example 1 uses concentrated hydrochloric acid; (e) a paper in the J. Org. Chemistry, 1985, (50) 3612 indicates that the reaction of 4-trifluoromethyl-2-nitro aniline with hydrochloric acid can lead to the formation of 4-trifluoromethyl-2-chloroaniline. Such a reaction could at least partly account for the low yields seen with the use of concentrated hydrochloric acid in the diazotization step.

OBJECT OF THE INVENTION

The object of the invention is to provide a facile and improved process for the preparation of 5-perfluoroalkyl substituted 2H-benzotriazole UV absorbers.

DETAILED DESCLOSURE

By contrast, the instant process describes an improved process for the preparation of 5-perfluoroalkyl (preferably trifluoromethyl) substituted 2H-benzotriazoles where in the diazotization step aqueous alkali metal (preferably sodium) nitrite and concentrated hydrochloric acid are replaced by aqueous alkali metal (preferably sodium) nitrite and concentrated sulfuric acid; and most preferably where aqueous alkali metal (sodium) nitrite and concentrated sulfuric acid are replaced with anhydrous nitrosylsulfuric acid with concentrated sulfuric acid as a diluent to allow operation at safe concentrations.

The instant invention more specifically pertains to a process for preparing a compound of formula I

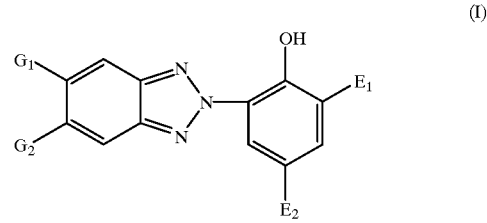

wherein
$G_1$ is hydrogen or chloro,
$G_2$ is perfluoroalkyl of 1 to 12 carbon atoms,
$E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_1$ is alkyl of 1 to 24 carbon atoms substituted by one or two hydroxy groups,
$E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —$OCOE_{11}$, —$OE_4$, —NCO, —$NHCOE_{11}$ or —$NE_7E_8$, or mixtures thereof, where $E_4$ is straight or branched chain alkyl of 1 to 24 carbon atoms; alkenyl of 2 to 18 carbon atoms; or said alkyl or said alkenyl interrupted by one or more —O—, —NH— or —$NE_4$— groups or mixtures thereof and which can be unsubstituted or substituted by one or more —OH, —$OE_4$ or —$NH_2$ groups or mixtures thereof; or $E_2$ is —$(CH_2)_m$—CO—$E_5$;
$E_5$ is $OE_6$ or $NE_7E_8$, or
$E_5$ is —$PO(OE_{12})_2$, —$OSi(E_{11})_3$ or —OCO—$E_1$, or straight or branched chain $C_1$–$C_{24}$alkyl which can be interrupted by —O—, —S— or —$NE_{11}$ and which can be unsubstituted or substituted by —OH or —OCO—$E_{11}$, $C_5$–$C_{12}$ cycloalkyl which is unsubstituted or substituted by —OH, straight chain or branched $C_2$–$C_{18}$alkenyl which is unsubstituted or substituted by —OH, $C_7$–$C_{15}$aralkyl, —$CH_2$—CHOH—$E_{13}$ or glycidyl,
$E_6$ is hydrogen, straight or branched chain $C_1$–$C_{24}$alkyl which is unsubstituted or substituted by one or more OH, $OE_4$ or $NH_2$ groups, or —$OE_6$ is —$(OCH_2CH_2)_wOH$ or —$(OCH_2CH_2)_wOE_{21}$where w is 1 to 12 and $E_{21}$ is alkyl of 1 to 12 carbon atoms,
$E_7$ and $E_8$ are independently hydrogen, alkyl of 1 to 18 carbon atoms, straight or branched chain alkenyl of 2 to 18 carbon atoms, straight or branched chain $C_3$–$C_{18}$alkyl which is interrupted by —O—, —S— or —$NE_{11}$—, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring,
$E_5$ is —X—$(Z)_p$—Y—$E_{15}$ wherein
X is —O— or —$N(E_{16})$—,
Y is —O— or —$N(E_{17})$—,
Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is zero, 1 or 2, p is 1, or p is also zero when X and Y are —N($E_{16}$)— and —N($E_{17}$)—, respectively, $E_{15}$ is a group —CO—C($E_{18}$)=C(H)$E_{19}$ or, when Y is —N($E_{17}$)—, forms together with $E_{17}$ a group —CO—CH=CH—CO—, wherein $E_{18}$ is hydrogen or methyl, and $E_{19}$ is hydrogen, methyl or —CO—X—$E2_0$, wherein $E_{20}$ is hydrogen, $C_1$–$C_{12}$-alkyl or a group of the formula

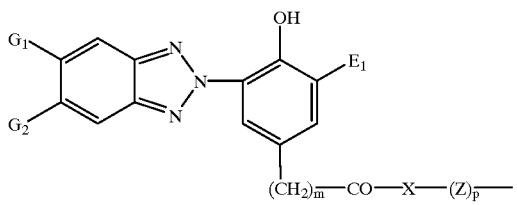

wherein the symbols $E_1$, $G_2$, X, Z, m and p have the meanings defined above, and $E_{16}$ and $E_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $E_{16}$ together with $E_{17}$ in the case where Z is ethylene, also forms ethylene, $E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_7$–$C_{15}$aralkyl, $E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, and $E_{13}$ is H, straight chain or branched $C_1$–$C_{18}$alkyl which is substituted by —PO(O$E_{12}$)$_2$, phenyl which is unsubstituted or substituted by OH, $C_7$–$C_{15}$aralkyl or —CH$_2$O$E_{12}$, which comprises diazotizing a perfluoroalkyl substituted o-nitroaniline of formula II (II)

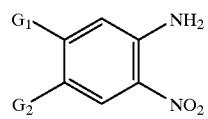

using concentrated sulfuric acid and an alkali metal nitrite (preferably sodium nitrite) or nitrosylsulfuric acid (most preferably nitrosylsulfuric acid) to form the corresponding diazonium salt of formula III (III)

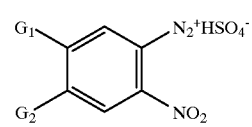

which then couples with a phenol of formula IV (IV)

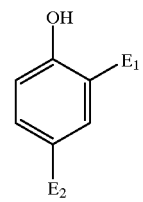

to form a monoazobenzene compound of formula V (V)

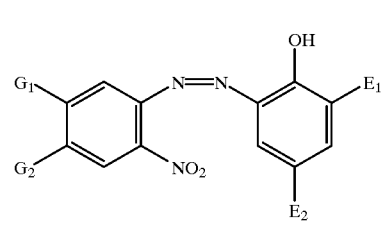

reducing the monoazobenzene intermediate of formula V to the corresponding 2H-benzotriazole compound of formula I by conventional reduction means; and with the proviso that when concentrated sulfuric acid and alkali metal nitrite are used, $E_1$ and $E_2$ are alkyl of 1 to 4 carbon atoms; or $E_1$ can also be hydrogen.

Preferably, the instant process involves the preparation of a compound of formula (Ia)

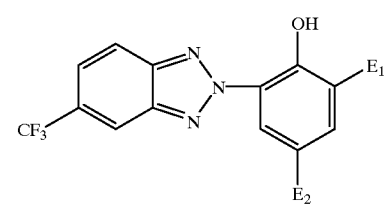

which comprises diazotizing a substituted o-nitroaniline compound of formula IIa (IIa)

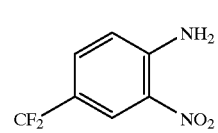

using concentrated sulfuric acid and sodium nitrite or nitrosylsulfuric acid to form the diazonium salt of formula IIIa (IIIa)

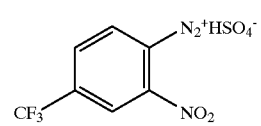

which then couples with a phenol of formula IV

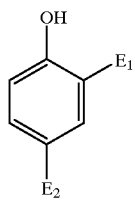

(IV)

to form the corresponding monoazobenzene compound of formula Va

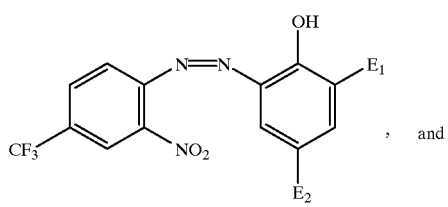

, and (Va)

reducing the monoazobenzene intermediate of formula Va to the corresponding 2H-benzotriazole compound of formula Ia by conventional reduction means; and with the proviso that when concentrated sulfuric acid and alkali metal nitrite are used, $E_1$ and $E_2$ are alkyl of 1 to 4 carbon atoms; or $E_1$ can also be hydrogen.

Preferably, in the compound of formula I, $G_1$ is hydrogen, $G_2$ is $CF_3$—, $E_1$ is phenylalkyl of 7 to 15 carbon atoms, phenyl, or said phenyl or said phenylalkyl substituted on the phenyl ring by one to three alkyl of 1 to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —OCOE$_{11}$, —OE$_4$, —NCO, —NH$_2$, —NHCOE$_{11}$, —NHE$_4$ or —N(E$_4$)$_2$, or mixtures thereof, where $E_4$ is straight or branched chain alkyl of 1 to 24 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof; or is a compound of formula I wherein, $G_1$ is hydrogen, $G_2$ is $CF_3$—, $E_1$ is hydrogen or straight or branched alkyl of 4 to 24 carbon atoms, and $E_2$ is as defined above.

Preferably, the compound of formula I is also where $G_1$ is hydrogen, $G_2$ is is $CF_3$—, $E_1$ is hydrogen, straight or branched alkyl of 4 to 24 carbon atoms or phenylalkyl of 7 to 15 carbon atoms, $E_2$ is —(CH$_2$)$_m$—CO—E$_5$, $E_5$ is —OE$_6$ or —NE$_7$E$_8$, or $E_5$ is —X—(Z)$_p$—Y—E$_{15}$ wherein X is —O— or —N(E$_{16}$)—, Y is —O— or —N(E$_{17}$)—, Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is 0, 1, 2 or 3, p is 1, or p is also zero when X and Y are —N(E$_{16}$)— and —N(E$_{17}$)—, respectively, $E_{15}$ is a group —CO—C(E$_{18}$)=C(H)E$_{19}$ or, when Y is —N(E$_{17}$)—, forms together with E$_{17}$ a group —CO—CH=CH—CO—, wherein E$_{18}$ is hydrogen or methyl, and E$_{19}$ is hydrogen, methyl or —CO—X—E$_{20}$, wherein E$_{20}$ is hydrogen, $C_1$–$C_{12}$-alkyl or a group of the formula.

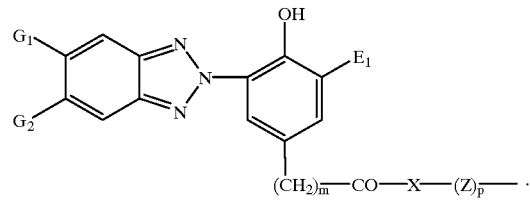

More preferably, the compound of formula I is where $G_1$ is hydrogen, $G_2$ is $CF_3$—, $E_1$ is phenylalkyl of 7 to 15 carbon atoms, phenyl, or said phenyl or said phenylalkyl substituted on the phenyl ring by one to three alkyl of 1to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —OCOE11, —NH$_2$ or —NHCOE$_{11}$, or mixtures thereof, or said alkyl or said alkenyl interrupted by one or more —O— and which can be unsubstituted or substituted by one or more —OH; or is a compound of formula I wherein, $G_1$ is hydrogen, $G_2$ is $CF_3$—, $E_1$ is hydrogen, straight or branched alkyl of 4 to 24 carbon atoms or phenylalkyl of 7 to 15 carbon atoms, and $E_2$ is as defined above.

Still more preferably, the compound of formula I is where $G_1$ is hydrogen, $G_2$ is $CF_3$—, $E_1$ is hydrogen, straight or branched alkyl of 4 to 24 carbon atoms or phenylalkyl of 7 to 15 carbon atoms, $E_2$ is (CH$_2$)$_m$—CO—E$_5$, $E_5$ is —OE$_6$ or —NE$_7$E$_8$ where $E_6$ is hydrogen, straight or branched chain $C_1$–$C_{24}$alkyl which is unsubstituted or substituted by one or more OH groups, or —OE$_6$ is —(OCH$_2$CH$_2$)$_w$OH or —(OCH$_2$CH$_2$)$_w$OE$_{21}$ where w is 1 to 12 and E$_{21}$ is alkyl of 1 to 12 carbon atoms, and E$_7$ and E$_8$ are independently hydrogen, alkyl of 1 to 18 carbon atoms, straight or branched chain C$_3$–C$_{18}$alkyl which is interrupted by —O—, —S— or —NE$_{11}$—, C$_5$–C$_{12}$cycloalkyl, C$_6$–C$_{14}$aryl or C$_1$–C$_3$hydroxylalkyl, or E$_7$ and E$_8$ together with the N atom are a pyrrolidine, piperidine, piperazine or morpholine ring.

Illustrative of the compounds of formula I which can be made by the instant process are (a) 5-trifluoromethyl-2-(2-hydroxy-3-(α-cumyl-5-tert-octylphenyl)-2H-benzotriazole;

(b) 5-trifluoromethyl-2-(2-hydroxy-5-tert-octylphenyl)-2H-benzotriazole;

(c) 5-trifluoromethyl-2-(2-hydroxy-3,5-di-tert-octylphenyl)-2H-benzotriazole;

(d) 5-trifluoromethyl-2-[2-hydroxy-5-(2-hydroxyethyl)phenyl]-2H-benzotriazole;

(e) 5-trifluoromethyl-2-(2-hydroxy-3,5-di-α-cumylphenyl)-2H-benzotriazole;

(f) 3-(5-trifluoromethyl-2H-benzotriazol-2-yl)-5-tert-butyl-4-hydroxyhydrocinnamic acid;

(g) methyl 3-(5-trifluoromethyl-2H-benzotriazol-2-yl)-5-tert-butyl-4-hydroxyhydrocinnamate;

(h) isooctyl 3-(5-trifluoromethyl-2H-benzotriazol-2-yl)-5-tert-butyl-4-hydroxyhydrocinnamate;

(i) 5-trifluoromethyl-2-[2-hydroxy-5-(3-hydroxypropyl)phenyl]-2H-benzotriazole;

(j) 5-trifluoromethyl-2-[2-hydroxy-5-(3-acryloyloxypropyl)phenyl]-2H-benzotriazole;

(k) 5-trifluoromethyl-2-[2-hydroxy-5-(3-methacryloyloxypropyl)phenyl]-2H-benzotriazole;

(l) 5-trifluoromethyl-2-[2-hydroxy-5-(3-acrylylaminopropyl)phenyl]-2H-benzotriazole;

(m) 5-trifluoromethyl-2-[2-hydroxy-5-(3-methacrylylaminopropyl)phenyl]-2H-benzotriazole;

(n) 5-trifluoromethyl-2-(2-hydroxy-3-x-cumyl-5-tert-butylphenyl)-2H-benzotriazole;

(o) 5-trifluoromethyl-2-(2-hydroxy-3-x-cumyl-5-nonylphenyl)-2H-benzotriazole;

(p) 5-trifluoromethyl-2-[2-hydroxy-3-(x-cumyl-5-(2-hydroxyethyl)phenyl]-2H-benzotriazole;

(q) 5-trifluoromethyl-2-[2-hydroxy-3-ox-cumyl-5-(3-hydroxypropyl)phenyl]-2H-benzotriazole;

(r) 5-trifluoromethyl-2-(2-hydroxy- 3,5-ditert-amylphenyl)-2H-benzotriazole;

(s) 5-trifluoromethyl-2-(2-hydroxy- 3,5-ditert-butylphenyl)-2H-benzotriazole;

(t) 5-trifluoromethyl-2-(2-hydroxy-3-dodecyl-5-methylphenyl)-2H-benzotriazole;

(u) 5-trifluoromethyl-2-[2-hydroxy-3-tert-butyl-5-(3-hydroxypropyl)phenyl)-2H-benzotriazole; and (v) 5-trifluoromethyl-2-[2-hydroxy-3-tert-butyl-5-(2-hydroxyethyl)phenyl]-2H-benzotriazole;

Most preferably, the instant process involves the preparation of a compound of formula Ib, which comprises

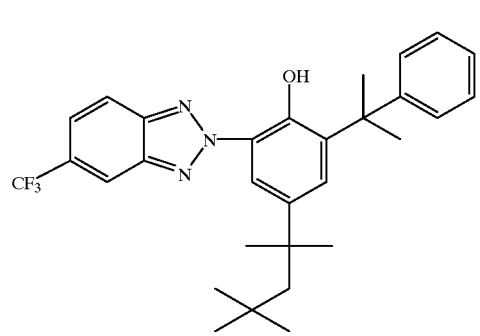

(Ib)

diazotizing a substituted o-nitroaniline compound of formula IIa

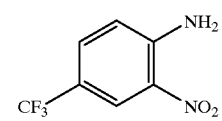

(IIa)

using nitrosylsulfuric acid to form the diazonium salt of formula IIIa

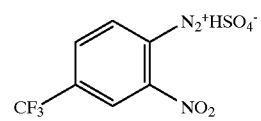

(IIIa)

which then couples with a phenol of formula IVa

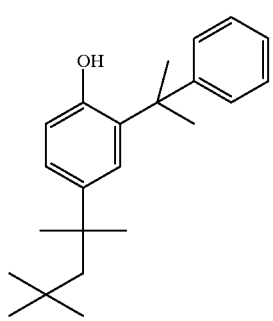

(IVa)

to form the corresponding monoazobenzene compound of formula Vb

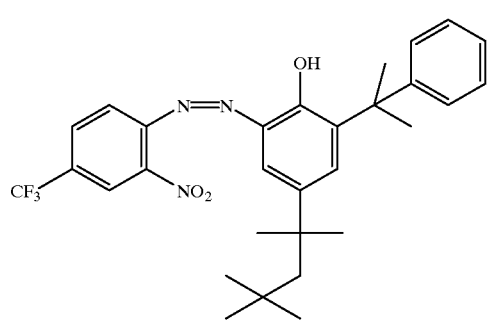

(Vb)

reducing the monoazobenzene intermediate of formula Vb to the corresponding 2H-benzotriazole compound of formula Ib by conventional reduction means.

Most preferably, the instant process involves the preparation of a compound of formula Ic, which comprises (Ic)

[Structure: 5-trifluoromethyl-2H-benzotriazole substituted with 2-hydroxy-5-(1,1,3,3-tetramethylbutyl)phenyl group]

diazotizing a substituted o-nitroaniline compound of formula IIa (IIa)

[Structure: 4-trifluoromethyl-2-nitroaniline]

using nitrosylsulfuric acid to form the diazonium salt of formula IIIa (IIIa)

[Structure: diazonium salt $N_2^+HSO_4^-$ of 4-trifluoromethyl-2-nitrobenzene]

which then couples with a phenol of formula IVa (IVc)

[Structure: 4-(1,1,3,3-tetramethylbutyl)phenol]

to form the corresponding monoazobenzene compound of formula Vc (Vc)

[Structure: monoazobenzene intermediate]

reducing the monoazobenzene intermediate of formula Vc to the corresponding 2H-benzotriazole compound of formula Ic by conventional reduction means.

Ia. In the process for making the diazonium salts using a perfluoroalkyl substituted o-nitroaniline (i.e. 4-trifluoromethyl-2-nitroaniline, $CF_3$—ONA), sulfuric acid and an aqueous alkali metal nitrite (i.e. sodium nitrite) solution, the following process parameters pertain:

a. The molar ratio of $CF_3$—ONA:sulfuric acid is 1:10 to 1:1; preferably 1:5 to 1:1; and most preferably 1:2–3.5.

b. The molar ratio of $CF_3$—ONA:sodium nitrite is 1:1 to 1:4; preferably 1:1 to 1:2; most preferably 1:1.

c. The temperature used for this reaction is from −30° C. to 50° C.; preferably from −20° C. to 20° C.; most preferably from −10° C. to 5° C.

Ib. In the process for making the diazonium salts using a perfluoroalkyl substituted o-nitroaniline (i.e. 4-trifluoromethyl-2-nitroaniline, $CF_3$—ONA) and nitrosylsulfuric acid in sulfuric acid, the following process parameters pertain:

a. The molar ratio of $CF_3$—ONA:nitrosylsulfuric acid is 1:1 to 1:2; preferably 1:1 to 1:1.2; and most preferably 1:1.

b. The molar ratio of $CF_3$—ONA:sulfuric acid is 1:1 to 1:10; preferably 1:2 to 1:7; most preferably 1:2 to 1:5.

c. The temperature used for this reaction is from −30° C. to 50° C.; preferably from −20° C. to 40° C.; most preferably from 0° C. to 25° C.

When preparing a diazonium salt using nitrosylsulfuric acid, a very low amount of water is required. The system is essentially anhydrous. When sulfuric acid concentrations are under 90%, nitrosylsulfuric acid becomes nitric oxide (NO) and evolves as a gas before it has time to react with the $CF_3$—ONA. At the end of the diazotization reaction, the diazonium salt solution in sulfuric acid is diluted with water to about 20–25%.

II. For the preparation of the monoazobenzene intermediate, there are two different coupling methods possible. The alkaline coupling method is described in detail in U.S. Pat. Nos. 4,275,004 and 4,347,180 which are incorporated herein by reference.

The acidic coupling process is described in detail in U.S. Pat. No. 5,436,322 which is incorporated herein by reference.

It is noted that instant Example 9 shows a coupling method which neither strongly alkaline nor strongly acidic. Rather, this Example shows coupling which is buffered with acetic acid and sodium hydroxide.

The details of the more preferred acidic coupling method are described infra.

The diazonium salt formed as described above is reacted with the appropriate phenol in a solvent containing a surface active modifier at a temperature of −30° C. to 75° C.; preferably at −20° C. to 50° C.; most preferably at −10° C. to 35° C.

The solvents used are water, an aromatic hydrocarbon, an aliphatic hydrocarbon or a mixture thereof. Preferably, the solvent is water, toluene, o-xylene, m-xylene, p-xylene or a mixture of said xylenes, mesitylene, pseudocumene, hexane, heptane, octane, nonane or a mixture thereof. Most preferably, the solvent is water, toluene, o-xylene, m-xylene, p-xylene, a mixture of said xylenes, heptane or a mixture thereof.

The amount of solvent to be used is that sufficient to dissolve the reactants. The amount of solvent is not critical, but making the solution too dilute is to be avoided.

The surface active modifier to be used is any one or a mixture of materials selected from the group consisting of emulsifying agents, surfactants, phase transfer agents and dispersants.

Preferably, the surfactive modifier is HOSTAPUR® SAS93 (Hoechst) or PETROSUL® M-60 (Penreco). The amount used is that needed to ensure adequate mixing of the reactants.

The molar ratio of diazonium salt:phenol is 2:1 to 1:2; preferably 1.5:1 to 1:1.5; most preferably 1:1.

III. The monoazobenzene compounds prepared in the instant process can be conveniently reduced to the corresponding benzotriazolyl-1-oxide and then to the corresponding 2H-benzotriazole by any number of conventional reduction methods. An illustrative list of such methods is given below, but should not be construed as being the only methods possible for carrying out said reduction.

1. EP 0380840 A1 describes the hydrogenation of a benzotriazolyl-1-oxide to the benzotriazole using palladium/carbon catalyst in toluene/water and in the presence of dimethylamine.

2. EP 0380840 A1 also discloses the hydrogenation of a benzotriazolyl-1-oxide to the benzotriazole using Raney nickel catalyst in toluene/2-butanol and in the presence of 1,5-diazabicyclo[5.4.0]undecane.

3. EP 0380839 A1 discloses the hydrogenation of a nitromonoazobenzene to the benzotriazole using Raney nickel catalyst in toluene/isopropanol and in the presence of sodium hydroxide.

4. EP 0380839 A1 also discloses the hydrogenation of a nitromonoazobenzene to the benzotriazole using palladium/carbon catalyst in toluene/water/isopropanol and in the presence of dimethylamine.

5. Japanese Sho 37-5934 (1962) and U.S. Pat. No. 3,773,751 describe the reduction of a nitromonoazobenzene to the benzotriazole using zinc, sodium hydroxide in an alcohol.

6. U.S. Pat. No. 2,362,988 discloses a variety of methods for the reduction of a nitromonoazobenzene to a benzotriazole. These include the use of:
   a. ammonium sulfide;
   b. an alkali metal sulfide;
   c. zinc and ammonia;
   d. hydrogen sulfide and sodium; or
   e. zinc and hydrochloric acid.

7. Japanese Sho 56-133076 (1981) describes the reduction of a nitromonoazo-benzene to a benzotriazole using quinone plus a variety of coreactants. These include:
   a. zinc;
   b. ammonium sulfide;
   c. alkali metal sulfide;
   d. alkali metal hydrosulfide; or
   e. hydrazine.

8. Japanese Sho 52-113973 (1977) and Sho 52-113974 (1977) describe the hydrogenation of a nitromonoazobenzene to a benzotriazole using a precious metal catalyst in the presence of a base.

9. Japanese Sho 59-170172 (1984) and Sho 63-72682 (1988) describe the reduction of a nitromonoazobenzene to a benzotriazole using a quinone or an aromatic ketone in the presence of an alcohol and a base and with heating.

10. Japanese Sho 61-215378 (1986) describes the reduction of a nitromonoazobenzene or a benzotriazolyl-1-oxide benzotriazole to a benzotriazole using an aldehyde and aromatic ketone in the presence of a base.

11. Japanese Sho 63-72683 (1988) and U.S. Pat. No. 4,780,541 describe the reduction of a nitromonoazobenzene or a benzotriazolyl-1-oxide benzotriazole to a benzotriazole using a primary or secondary alcohol and an aromatic ketone in the presence of a base.

12. Japanese Sho 63-186886 (1988) describes the electrolytic reduction of a nitromonoazobenzene or a benzotriazolyl-1-oxide benzotriazole to a benzotriazole using an alkali metal hydroxide in water or an aqueous alcohol solution.

13. Japanese Sho 61-215379 (1986) and U.S. Pat. No. 4,789,541 describe the reduction of a benzotriazolyl-1-oxide benzotriazole to a benzotriazole using an aldehyde and an aromatic ketone in the presence of a base.

14. U.S. Pat. No. 5,571,924 describes the reduction of a nitromonoazobenzene or a benzotriazolyl-1-oxide benzotriazole to a benzotriazole using hydrazine and a precious metal catalyst.

15. U.S. Pat. No. 3,978,074 discloses the reduction of a nitromonoazobenzene to a benzotriazole using a hydrogen and a noble metal catalyst in the presence of an aqueous alkali metal hydroxide solution.

16. U.S. Pat. No. 4,219,480 discloses the reduction of a nitromonoazobenzene to a benzotriazole using a hydrogen and a Raney nickel catalyst in the presence of an aqueous alkali metal hydroxide solution or in the presence of an aliphatic amine.

17. U.S. Pat. No. 4,230,867 discloses the reduction of a nitromonoazobenzene to a benzotriazole using a hydrogen and a noble metal catalyst in the presence of an aliphatic amine.

The following examples are for illustrative purposes only and are not to be construed to limit the scope of the instant invention in any manner whatsoever.

There are four generic procedures outlined in the Examples illustrating various methods of making the diazonium salts which are used to produce the desired monoazobenzene compounds by coupling with the appropriate phenol.

EXAMPLE 1

2-Nitrobenzenediazonium Chloride

To a laboratory reactor equipped with the necessary auxiliary attachments is added 206.4 g (32% by weight, 1.81 mol) of hydrochloric acid. o-Nitroaniline (82.6 g, 0.60 mol, ONA, Aldrich Chemical Co.) is added slowly to the well-stirred solution. An exotherm temperature of 40–50° C. occurs. After dissolution of the ONA is complete, ice (104 g, 5.78 mol) is charged and cooling is applied. At a temperature of −15° C. to −10° C., sodium nitrite (37.5 g, 0.60 mol) is charged slowly over a one-hour period while maintaining the temperature at −15° C. to −10° C. The resulting solution is clarified through a bed of Solka Floc (ground cellulose). A light yellow aqueous diazonium chloride salt solution is obtained in a yield of 410 g and is stored at about −15° C. to −10° C. till later use.

EXAMPLE 2

5-Trifluoromethyl-2-nitrobenzenediazonium Chloride

Following a procedure similar to that of EXAMPLE 1, o-nitroaniline (ONA) is replaced with 4-trifluoromethyl-2-nitroaniline ($CF_3$—ONA). When 41.2 g of $CF_3$—ONA (Aldrich Chemical Co.) is used, the title compound is obtained in a yield of 205 g as an aqueous solution and is stored at −15° C. to −10° C. till later use.

EXAMPLE 3

5-Trifluoromethyl-2-nitrobenzenediazonium Bisulfate

To a laboratory reactor equipped with necessary ancillary equipment, 93% sulfuric acid (99.5 g, 0.94 mol) is charged. 4-Trifluoromethyl-2-nitroaniline (63.9 g, 0.30 mol, obtained from Aldrich Chemical Co.) is added slowly to the well-stirred reaction mass. The reaction mass is heated to 70–75° C. to ensure complete dissolution. At this temperature, water (200 g, 11.1 mol) is added slowly while maintaining the temperature at 70–75° C. The reaction mixture is cooled to 0–5° C. at which time sodium nitrite (54.3 g, 0.32 mol, as a 40% aqueous solution) is charged over a two-hour period. The temperature should be kept in this temperature range since an exotherm can occur if the temperature is not monitored carefully. The resulting yellow solution is clarified through a bed of Solka Floc (ground cellulose). The yellow aqueous diazonium salt solution (400 g) is obtained and stored at −15° C. to −10° C. till later use.

EXAMPLE 4

5-Trifluoromethyl-2-nitrobenzenediazonium Bisulfate

To a laboratory reactor equipped with the necessary ancillary equipment, nitrosylsulfuric acid (384.7 g, 1.20 mol, 40% solution in sulfuric acid, obtained from Aldrich Chemical Co. or synthesized before use) and concentrated 98% sulfuric acid (287.3 g, 2.73 mol) are charged. To the above solution well-stirred and cooled to 10–15° C., 4-trifluoromethyl-2-nitroaniline (250.7 g, 1.20 mol, obtained from Aldrich Chemical Co.) is charged portion-wise over one to two hours while maintaining the temperature at 0° C. Ice (700 g, 38.9 mol) is charged slowly and the excess nitrosylsulfuric acid is destroyed with sulfamic acid. The yellow solution formed is clarified through a sintered glass funnel. The reactor and funnel are rinsed with cold water (100 g, 5.6 mol) and combined with the diazonium salt solution. The title compound is prepared in a yield of 1777.9 g as a yellow, aqueous solution which is stored at −15° C. to −10° C. until later use.

Examples 5–12 show the preparation of selected monoazobenzene compounds which are intermediates for preparing the corresponding 2H-benzotriazole UV abosrbers.

EXAMPLE 5

2-Hydroxy-2'-nitro-4'-trifluoromethyl-5-tert-octylazobenzene

To a laboratory reactor equipped with the necessary auxiliary equipment, 4-tert-octylphenol (36.0 g, 0.17 mol, obtained from Aldrich Chemical Co.), xylenes (90 g, 0.84 mol) and HOSTAPUR® SAS93 (1.5 g, surfactant, Hoechst Corp.) are charged. The reaction mixture is cooled to 10° C. at which time the diazonium salt solution, prepared in Example 2, (303 g, 0.17 mol, as a 14.3% solution) is charged over a three-hour period. The aqueous layer is separated after heating the reaction mass to 45° C. The xylene phase is analyzed for the title compound; standardized HPLC analysis reveals a 23.7% yield of the title compound.

EXAMPLE 6

2-Hydroxy-2'-nitro-4'-trifluoromethyl-3,5-di-tert-butylazobenzene

To a laboratory reactor equipped with the necessary auxiliary equipment, 2,4-di-tert-butylphenol (47.1g, 0.22 mol, obtained from Schenectady Chemical Co.), xylenes (80 g, 0.75 mol) and PETROSUL® M-60 (1.8 g, surfactant, Penreco) are charged. At ambient temperature (20–25° C.), the diazonium salt solution prepared in Example 3 (344 g, 0.24 mol) is charged over a 4.25 hour period while continuing agitation for another six hours. Xylenes (300 g, 2.83 mol) and sodium hydroxide (183 g, 1.14 mol as a 25% aqueous solution) are charged while heating to 75° C. The aqueous layer is removed and the organic layer is subjected to vacuum distillation to remove xylenes. The crimson red oil obtained is crystallized from 120 g of methanol at 0° C. The solids are filtered and washed with 300 g of cold methanol. After vacuum drying, the title compound is prepared in 86.8% yield (82.3 g) as a solid melting at 105° C. The structure is verified by $^1$Hnmr and mass spectrometry analyses.

EXAMPLE 7

2-Hydroxy-2'-nitro-4'-trifluoromethyl-4,5-dimethylazobenzene (major)

2-Hydroxy-2'-nitro-4'-trifluoromethyl-5,6-dimethylazobenzene (minor)

Following the procedure of EXAMPLE 6, 3,4-dimethylphenol (27.8 g, 0.23 mol) is substituted for 2,4-di-tert-butylphenol. The title compounds are obtained as 67.4 g, 86.4% yield as a crimson solid and is a 83:17 mixture of the two indicated regioisomers as judged by $^1$Hnmr analysis.

EXAMPLE 8

2-Hydroxy-2'-nitro-5-methylazobenzene

To a laboratory reactor equipped with the necessary auxiliary equipment, water (698 g, 38.8 mol), sodium hydroxide (49.2 g, 0.61 mol as a 50% aqueous solution) and p-cresol (66.9 g, 0.62 mol) are charged. After cooling to 0° C., the diazonium salt solution prepared in Example 1(444 g, 0.60 mol as a 25% aqueous solution) is added over 3.5 hours. During the latter two hours of addition a pH of 8.0–9.0 is maintained (47.6 g of 50% aqueous sodium hydroxide is required.). Xylenes (310 g, 2.92 mol) and water (150 g, 8.33 mol) are charged while heating the solution to 84–86° C. The aqueous layer is removed and the organic layer is washed once with 300 g of water. The xylene phase is dried by azeotropic distillation. The title compound is obtained as a crimson red xylene solution (370 g, 96.1% yield as a 40% by weight solution).

EXAMPLE 9

2-Hydroxy-2'-nitro-4'-trifluoromethyl-5-tert-octylazobenzene

To a laboratory reactor equipped with the necessary ancillary equipment, xylenes (188.4 g, 1.78 mol), methanol (5.4 g, 0.17 mol), water (120 g, 6.67 mol), acetic acid (60 g, 1.0 mol) and p-tert-octylphenol (56.9 g, 0.28 mol) are charged. After cooling to −5° C., the diazonium salt solution prepared in EXAMPLE 4 (424.2 g, 0.27 mol as a 19.7% aqueous solution) and sodium hydroxide (473 g, 2,37 mol as a 20% aqueous solution) are charged simultaneously over three hours. A thirty gram water rinse is charged after completion of the diazonium salt solution addition. The reaction mass is allowed to warm to 520 C. over two hours with continued stirring. Xylenes (50 g, 0.47 mol) is added following by heating to 40° C. The water phase is split off and the desired product is isolated from the xylene phase. The title compound is prepared as a crimson solid (82.7 g, 73.8% yield) whose structure is consistent with $_1$Hnmr analysis.

EXAMPLE 10

2-Hydroxy-2'-nitro-4'-trifluoromethyl-3-α-cumyl-5-tert-octylazobenzene

To a laboratory reactor equipped with the necessary ancillary equipment, xylenes (411.7 g, 3.88 mol), 2-α- cumyl-4-tert-octylphenol (232.8 g, 0.69 mol) and HOSTA-PUR® SAS 93 (9.7 g, surfactant, Hoechst Corp.) are charged. After cooling to 0–5° C., the diazonium salt solution prepared in Example 4 (1115.4 g, 0.68 mol)is added over a 3.75 hour period. While the diazonium salt solution is added, the reaction mass is homogenized with an Ultra-turax homogenizer. After the diazonium salt solution addition is complete, agitation is continued for another two hours. The reaction mass is heated to 55° C. and the aqueous layer is split off. From the organic phase, the title compound is obtained as a crimson red solid (282.9 g, 76.4% yield) melting at 101–105° C.

Examples 6 and 7 show that the diazonium salts produced using sulfuric acid and sodium nitrite as seen in Example 3 are useful for coupling with phenols having lower alkyl substitution (such as 3,4-dimethylphenol in Example 7 or 2,4-di-tert-butylphenol in Example 6). Examples 11and 12 show that diazonium salts as prepared in Example 3 are not useful for coupling with phenols having longer alkyl chains (such as 4-tert-octylphenol) even though 2,4-di-tert-butylphenol and 4-tert-octylphenol have the same total number of alkyl carbon atoms as substituents.

EXAMPLE 11

2-Hydroxy-2'-nitro-4'-trifluoromethyl-5-tert-octylazobenzene

To a laboratory reactor equipped with the necessary auxiliary equipment, xylenes (201.4 g, 1.90 mol), p-tert-octylphenol (82.6 g, 0.39 mol) and HOSTAPUR® SAS 93 (3.4 g, surfactant, Hoechst Corp.) are charged. After cooling to 10–12° C., the diazonium salt solution prepared in Example 3 (874.9 g, 0.39 mol as a 14.05% aqueous solution) is added over a three-hour period. The reaction mass is heated to 25° C. and the aqueous layer is removed. The title compound is obtained from the xylene phase as a crimson solid in a yield of 61.47 g (37% yield).

EXAMPLE 12

2-Hydroxy-2'-nitro-4'-trifluoromethyl-5-tert-octylazobenzene

To a laboratory reactor equipped with the necessary auxiliary equipment, xylenes (15.3 g, 0.14 mol), p-tert-octylphenol (32.5 g, 0.15 mol), methanol (237.6 g, 7.42 mol), water (7.0 g, 0.39 mol) and sodium hydroxide (63.6 g, 1.59 mol) are added. The temperature is reduced to −15° C. to −10° C. at which time the diazonium salt solution prepared in Example 3 (311.2 g, 0.195 mol as a 19.8% aqueous solution) is added over a four-hour period. Water (190 g, 10.6 mol) and xylenes (304.5 g, 2.87 mol) are added while heating to 65° C. The aqueous layer is removed. The title compound is isolated from the xylene phase as a crimson solid in a yield of 21.6 g (33.8% yield).

Examples 5, 9, 11and 12 show the synthesis of the same monoazo compound, namely 2-hydroxy-2'-nitro-4'-trifluoromethyl-5-tert-octylazobenzene, from the diazonium salt prepared from 4-trifluoro-2-nitroaniline (CF$_3$—ONA) and coupled with 4-tert-octylphenol. The diazonium salt solutions are prepared by different preparative methods as shown in Examples 2, 3 and 4. The yields for preparing the monoazo compounds are tabulated in the Table below showing that when a trifluoromethyl moiety is present that major differences in yield occur depending on how the diazonium salt is prepared regardless of the coupling method.

| Diazonium Salt of Example | Method of Making Diazonium Salt | Monoazo Yield (%) |
|---|---|---|
| 5 | NaNO$_2$ + HCl | 23.7 |
| 11 | NaNO$_2$ + H$_2$SO$_4$ | 37* |
| 12 | NaNO$_2$ + H$_2$SO$_4$ | 33.8** |
| 9 | nitrosylsulfuric | 73.8 |
| 10*** | nitrosylsulfuric | 76.4 |

*Acid coupled
**Base coupled
***The monoazo compound is 2-hydroxy-2'-nitro-3-α-cumyl-4'-trifluoromethyl-5-tert-octylazobenzene.

It is clear that the use of nitrosylsulfuric acid in the preparation of the diazonium salt where a trifluoromethyl moiety is present leads to far superior yields of the key monoazobenzene intermediate needed to prepare the instant benzotriazole UV absorbers.

When the monoazo compound is 2-hydroxy-2'-nitro-4'-trifluoromethyl-3,5-di-tert-butylazobenzene as seen in Example 6, the method of making the monoazo compound using NANO$_2$ +H$_2$SO$_4$ leads to a yield of 86.8% in contrast to the yields of 37% and 33.8% when the monoazo compound is 2-hydroxy-2'-nitro-4'-trifluoromethyl-5-tert-octylazobenzene made using NaNO$_2$ +H$_2$SO$_4$ as seen in Examples 11and 12.

Examples 13 and 14 show that the monoazobenzene compounds of the instant invention can be reduced to the desired 2H-benzotriazole UV absorber in excellent yield using any of a number of conventional methods such as, for example, by catalytic hydrogenation using hydrogen in a basic medium or reduction using 2,3-dichloro-1,4-naphthoquinone.

EXAMPLE 13

5-Trifluoromethyl-2-(2-hydroxy-5-tert-octylphenyl)-2H-benzotriazole

To a laboratory autoclave equipped with the necessary auxiliary equipment, the monoazo compound prepared in Example 9 (112.4 g, 0.25 mol), xylenes (160 g, 1.51 mol), n-butylamine (110 g, 1.50 mol) and platinum/palladium on carbon catalyst (1.5 g, Johnson Matthey Co.) are added. At a temperature of 20–25° C., hydrogen is metered slowly into the autoclave at a pressure of 30 psig. At the end of the reaction, the final reaction temperature is adjusted to 55° C. The hydrogen is vented and the catalyst is removed by filtration. The n-butylamine is removed by distillation and the reaction mass is cooled to 60° C. at which time it is washed with 134.5 g of 78% sulfuric acid. After splitting off the acid phase, the organic phase is washed twice with 200 g of water at 65–75° C. The xylene phase is dried by azeotropic distillation and then treated with 5 g of acidic alumina. After removal of the alumina, the xylene is distilled and replaced with 200 g of methanol and seeded. The slurry is cooled to 0° C., filtered and washed with 200 g of methanol and dried overnight at 65° C. in a vacuum oven. The title compound is obtained as a white powder (71.8 g, 71.6% yield) with a melting point of 80–81° C.

EXAMPLE 14

5-Trifluoromethyl-2-(2-hydroxy-3-α-cumyl-5-tert-octylphenyl)-2H-benzotriazole

To a laboratory reactor equipped with the necessary auxiliary equipment, 2-butanol (700 g, 9.46 mol) and sodium hydroxide pellets (23.7 g, 0.59 mol) are charged and heated to reflux. A solution of the monoazo compound prepared in Example 10 (122.4 g, 0.22 mol), 2,3-dichloro-1,4-naphthoquinone (5.6 g, 0.025 mol from the Aldrich Chemical Co.), heptane (342 g, 3.41 mol) and methyl ethyl ketone (402.5 g, 5.6 mol) is added to the refluxing solution over a two-hour period while distilling off methyl ethyl ketone and heptane. After the reaction is complete, the temperature is reduced to 45–50° C. at which time the reaction mass is neutralized with 30% aqueous sulfuric acid. The temperature is reduced to 25° C. and the reaction mass is seeded. After cooling to 5° C., the slurry is filtered and washed with 232 g of hot water. The filter cake is allowed to cool to ambient temperature and is then washed with 200 g of cold methanol and dried in a vacuum oven. The title compound is prepared in a yield of 92.8 g, 79.1% yield and has a melting point of 119–121° C.

What is claimed is:

1. A process for preparing a compound of formula I

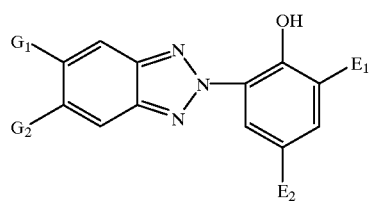

(I)

wherein $G_1$ is hydrogen or chloro, $G_2$ is perfluoroalkyl of 1 to 12 carbon atoms, $E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1to 4 carbon atoms; or $E_1$ is alkyl of 1 to 24 carbon atoms substituted by one or two hydroxy groups, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1to 4 carbon atoms; or $E_2$ is said alkyl of 1 to 24 carbon atoms or said alkenyl of 2 to 18 carbon atoms substituted by one or more —OH, —OCOE$_{11}$, —OE$_4$, —NCO, —NHCOE$_{11}$ or —NE$_7$E$_8$, or mixtures thereof, where $E_4$ is straight or branched chain alkyl of 1to 24 carbon atoms or alkenyl of 2 to 18 carbon atoms; or said alkyl or said alkenyl interrupted by one or more —O—, —NH—or —NE$_4$— groups or mixtures thereof and which can be unsubstituted or substituted by one or more —OH, —OE$_4$ or —NH$_2$ groups or mixtures thereof; or $E_2$ is —(CH$_2$)$_m$—CO—E$_5$;

$E_5$ is OE$_6$ or NE$_7$E$_8$, or $E_5$ is —PO(OE$_{12}$)$_2$, —OSi(E11)3 or —OCO—E$_{11}$, or straight or branched chain $C_1$–$C_{24}$alkyl which can be interrupted by —O—, —S—or —NE$_{11}$ and which can be unsubstituted or substituted by —OH or —OCO—E$_{11}$, $C_5$–$C_{12}$ cycloalkyl which is unsubstituted or substituted by —OH, straight chain or branched $C_2$–$C_{18}$alkenyl which is unsubstituted or substituted by —OH, $C_7$–$C_{15}$aralkyl, —CH$_2$—CHOH—E$_{13}$ or glycidyl, $E_6$ is hydrogen, straight or branched chain $C_1$–$C_{24}$alkyl which is unsubstituted or substituted by one or more OH, OE$_4$ or NH$_2$ groups, or —OE$_6$ is —(OCH$_2$CH$_2$)$_w$OH or —(OCH$_2$CH$_2$)$_w$OE$_{21}$where w is 1 to 12 and $E_{21}$is alkyl of 1to 12 carbon atoms, $E_7$ and $E_8$ are independently hydrogen, alkyl of 1to 18 carbon atoms, straight or branched chain alkenyl of 2 to 18 carbon atoms, straight or branched chain $C_3$–$C_{18}$alkyl which is interrupted by —O—, —S—or —NE$_{11}$—, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring, $E_5$ is —X—(Z)$_p$—Y—E$_{15}$ wherein X is —O— or —N(E$_{16}$)—, Y is —O— or —N(E$_{17}$)—, Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is zero, 1or 2, p is 1, or p is also zero when X and Y are —N(E$_{16}$)— and —N(E$_{17}$)—, respectively, $E_{15}$ is a group —CO—C(E$_{18}$)=C(H)E$_{19}$ or, when Y is —N(E$_{17}$)—, forms together with $E_{17}$ a group —CO—CH=CH—CO—, wherein $E_{18}$ is hydrogen or methyl, and $E_{19}$ is hydrogen, methyl or —CO—X—E$_{20}$, wherein $E_{20}$ is hydrogen, $C_1$–$C_{12}$-alkyl or a group of the formula

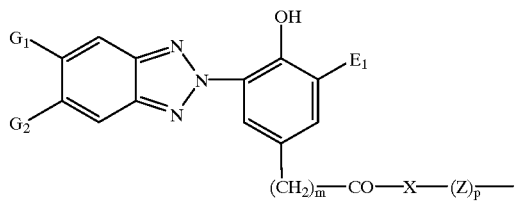

wherein the symbols $E_1$, $G_2$, X, Z, m and p have the meanings defined above, and $E_{16}$ and $E_{17}$ independently of one another are hydrogen, $C_1$–$C_{12}$-alkyl, $C_3$–$C_{12}$-alkyl interrupted by 1to 3 oxygen atoms, or is cyclohexyl or $C_7$–$C_{15}$aralkyl, and E16 together with $E_{17}$ in the case where Z is ethylene, also forms ethylene, $E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_7$–$C_{15}$aralkyl, $E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, and $E_{13}$ is H, straight chain or branched $C_1$–$C_{18}$alkyl which is substituted by —PO(OE$_{12}$)$_2$, phenyl which is unsubstituted or substituted by OH, $C_7$–$C_{15}$aralkyl or —CH$_2$OE$_{12}$, which comprises diazotizing a perfluoroalkyl substituted o-nitroaniline of formula II

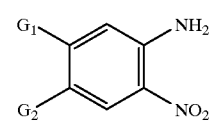

(II)

using concentrated sulfuric acid and an alkali metal nitrite or nitrosylsulfuric acid to form the corresponding diazonium salt of formula III

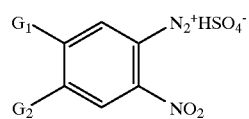 (III)

which then couples with a phenol of formula IV

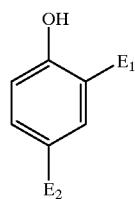 (IV)

to form a monoazobenzene compound of formula V

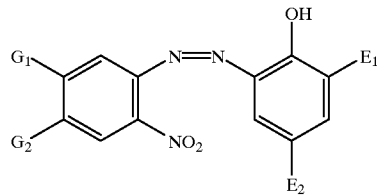 (V)

reducing the monoazobenzene intermediate of formula V to the corresponding 2H-benzotriazole compound of formula I by conventional reduction means; and with the proviso that when concentrated sulfuric acid and alkali metal nitrite are used, $E_1$ and $E_2$ are alkyl of 1 to 4 carbon atoms, or $E_1$ can also be hydrogen.

2. A process according to claim 1 wherein the alkali metal nitrite is sodium nitrite.

3. A process according to claim 1 wherein nitrosylsulfuric acid is used to diazotize the o-nitroaniline compound of formula II.

4. A process according to claim 1 for the preparation of a compound of formula Ia

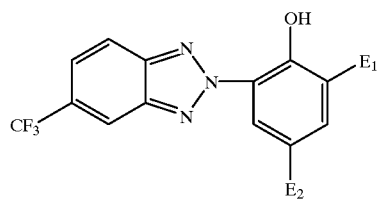 (Ia)

which comprises diazotizing a substituted o-nitroaniline compound of formula IIa

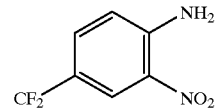 (IIa)

using concentrated sulfuric acid and sodium nitrite or nitrosylsulfuric acid to form the diazonium salt of formula IIIa

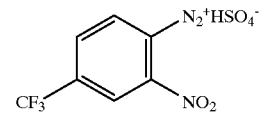 (IIIa)

which then couples with a phenol of formula IV

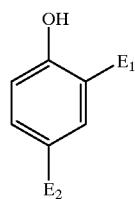 (IV)

to form the corresponding monoazobenzene compound of formula Va

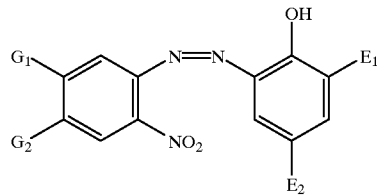 (Va)

, and reducing the monoazobenzene intermediate of formula Va to the corresponding 2H-benzotriazole compound of formula Ia by conventional reduction means; and with the proviso that when concentrated sulfuric acid and alkali metal nitrite are used, $E_1$ and $E_2$ are alkyl of 1 to 4 carbon atoms, or $E_1$ can also be hydrogen.

5. A process according to claim 1 where in the compound of formula I $G_1$ is hydrogen, $G_2$ is $CF_3$—, $E_1$ is phenylalkyl of 7 to 15 carbon atoms, phenyl, or said phenyl or said phenylalkyl substituted on the phenyl ring by one to three alkyl of 1 to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —OCOE$_{11}$, —OE$_4$, —NCO, —NH$_2$, —NHCOE$_{11}$, —NHE$_4$ or —N(E$_4$)$_2$, or mixtures thereof, where E$_4$ is straight or branched chain alkyl of 1 to 24 carbon atoms; or said alkyl or said alkenyl interrupted by one or more —O—, —NH—or —NE$_4$— groups or mixtures thereof and which can be unsubstituted or substituted by one or more —OH, —OE$_4$ or —NH$_2$ groups or mixtures thereof; or where in the compound of formula I G$_1$ is hydrogen, G$_2$ is CF$_3$—, E$_1$ is hydrogen or straight or branched alkyl of 4 to 24 carbon atoms, and E$_2$ is as defined above.

6. A process according to claim 1 where in the compound of formula I

G$_1$ is hydrogen,

G$_2$ is is CF$_3$—,

E$_1$ is hydrogen, straight or branched alkyl of 4 to 24 carbon atoms or phenylalkyl of 7 to 15 carbon atoms, E$_2$ is —(CH$_2$)$_m$—CO—E$_5$, E$_5$ is —OE$_6$ or —NE$_7$E$_8$, or E$_5$ is

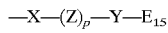

wherein

X is —O— or —N(E$_{16}$)—,

Y is —O— or —N(E$_{17}$)—,

Z is C$_2$–C$_{12}$-alkylene, C$_4$–C$_{12}$-alkylene interrupted by one to three nitrogen atoms, oxygen atoms or a mixture thereof, or is C$_3$–C$_{12}$-alkylene, butenylene, butynylene, cyclohexylene or phenylene, each substituted by a hydroxyl group, m is 0, 1, 2 or 3, p is 1, or p is also zero when X and Y are —N(E$_{16}$)— and —N(E$_{17}$)—, respectively, E$_{15}$ is a group —CO—C(E$_{18}$)═C(H)E$_{19}$ or, when Y is —N(E$_{17}$)—, forms together with E$_{17}$ a group —CO—CH═CH—CO—, wherein E$_{18}$ is hydrogen or methyl, and E$_{19}$ is hydrogen, methyl or —CO—X—E$_{20}$, wherein E$_{20}$ is hydrogen, C$_1$–C$_{12}$-alkyl or a group of the formula.

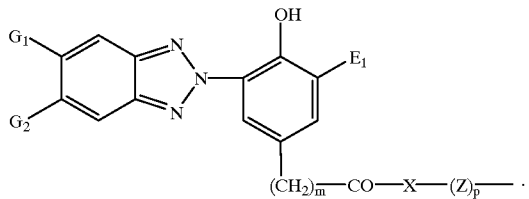

7. A process according to claim 1 where in the compound of formula I

G$_1$ is hydrogen,

G$_2$ is CF$_3$—,

E$_1$ is phenylalkyl of 7 to 15 carbon atoms, phenyl, or said phenyl or said phenylalkyl substituted on the phenyl ring by one to three alkyl of 1 to 4 carbon atoms, E$_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or E$_2$ is said alkyl of 1 to 24 carbon atoms or said alkenyl of 2 to 18 carbon atoms substituted by one or more —OH, —OCOE$_{11}$, —NH$_2$ or —NHCOE$_{11}$, or mixtures thereof, or said alkyl or said alkenyl interrupted by one or more —O— and which can be unsubstituted or substituted by one or more —OH, or where in the compound of formula I G$_1$ is hydrogen, G$_2$ is CF$_3$—, E$_1$ is hydrogen, straight or branched alkyl of 4 to 24 carbon atoms or phenylalkyl of 7 to 15 carbon atoms, and E$_2$ is as defined above.

8. A process according to claim 1 where in the compound of formula I

G$_1$ is hydrogen,

G$_2$ is CF$_3$—,

E$_1$ is hydrogen, straight or branched alkyl of 4 to 24 carbon atoms or phenylalkyl of 7 to 15 carbon atoms, E$_2$ is —(CH$_2$)$_m$—CO—E$_5$, E$_5$ is —OE$_6$ or —NE$_7$E$_8$ where E$_6$ is hydrogen, straight or branched chain C$_1$–C$_{24}$alkyl which is unsubstituted or substituted by one or more OH groups, or —OE$_6$ is —(OCH$_2$CH$_2$)$_w$OH or —(OCH$_2$CH$_2$)$_w$OE$_{21}$where w is 1 to 12 and E$_{21}$ is alkyl of 1 to 12 carbon atoms, and E$_7$ and E$_8$ are independently hydrogen, alkyl of 1 to 18 carbon atoms, straight or branched chain C$_3$–C$_{18}$alkyl which is interrupted by —O—, —S—or —NE$_{11}$—, C$_5$–C$_{12}$cycloalkyl, C$_6$–C$_{14}$aryl or C$_1$–C$_3$hydroxylalkyl, or E$_7$ and E$_8$ together with the N atom are a pyrrolidine, piperidine, piperazine or morpholine ring.

9. A process according to claim 1 wherein the compound of formula I is (a) 5-trifluoromethyl-2-(2-hydroxy-3-α-cumyl-5-tert-octylphenyl)-2H-benzotriazole;

(b) 5-trifluoromethyl-2-(2-hydroxy-5-tert-octylphenyl)-2H-benzotriazole;

(c) 5-trifluoromethyl-2-(2-hydroxy-3,5-di-tert-octylphenyl)-2H-benzotriazole;

(d) 5-trifluoromethyl-2- [2-hydroxy-5-(2- hydroxyethyl)phenyl]-2H-benzotriazole;

(e) 5-trifluoromethyl-2-(2-hydroxy-3,5-di-α-cumylphenyl)-2H-benzotriazole;

(f) 3-(5-trifluoromethyl-2H-benzotriazol-2-yl)-5-tert-butyl-4-hydroxyhydrocinnamic acid;

(g) methyl 3-(5-trifluoromethyl-2H-benzotriazol-2-yl)-5-tert-butyl-4-hydroxyhydrocinnamate;

(h) isooctyl 3-(5-trifluoromethyl-2H-benzotriazol-2-yl)-5-tert-butyl-4-hydroxyhydrocinnamate;

(i) 5-trifluoromethyl-2-[2-hydroxy-5-(3-hydroxypropyl)phenyl]-2H-benzotriazole;

(j) 5-trifluoromethyl-2-[2-hydroxy-5-(3-acryloyloxypropyl)phenyl]-2H-benzotriazole;

(k) 5-trifluoromethyl-2-[2-hydroxy-5-(3-methacryloyloxypropyl)phenyl]-2H-benzotriazole;

(l) 5-trifluoromethyl-2-[2-hydroxy-5-(3-acrylylaminopropyl)phenyl]-2H-benzotriazole;

(m) 5-trifluoromethyl-2-[2-hydroxy-5-(3-methacrylylaminopropyl)phenyl]-2H-benzotriazole;

(n) 5-trifluoromethyl-2-(2-hydroxy-3-(α-cumyl-5-tert-butylphenyl)-2H-benzotriazole;

(o) 5-trifluoromethyl-2-(2-hydroxy-3-(α-cumyl-5-nonylphenyl)-2H-benzotriazole;

(p) 5-trifluoromethyl-2–12-hydroxy-3-α-cumyl-5-(2-[2-hydroxy-3-α- cumyl- 5-(2-hydroxyethyl)phenyl]-2H-benzotriazole;

(q) 5-trifluoromethyl-2-[2-hydroxy-3-a-cumyl-5-(3-hydroxypropyl)phenyl]-
(r) 5-trifluoromethyl-2-(2-hydroxy-3,5-ditert-amylphenyl)-2H-benzotriazole;
(s) 5-trifluoromethyl-2-(2-hydroxy-3,5-ditert-butylphenyl)-2H-benzotriazole;
(t) 5-trifluoromethyl-2-(2-hydroxy-3-dodecyl-5-methylphenyl)-2H-benzotriazole;
(u) 5-trifluoromethyl-2-[2-hydroxy-3-tert-butyl-5-(3-hydroxypropyl)phenyl]-2H-benzotriazole; or
(v) 5-trifluoromethyl-2-[2-hydroxy-3-tert-butyl-5-(2-hydroxyethyl)phenyl]-2H-benzotriazole.

10. A process according to claim 1 for the preparation of a compound of formula Ib which comprises (Ib)

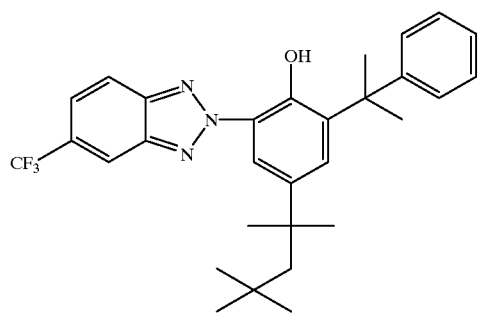

diazotizing a substituted o-nitroaniline compound of formula IIa (IIa)

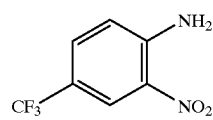

using nitrosylsulfuric acid to form the diazonium salt of formula IIIa (IIIa)

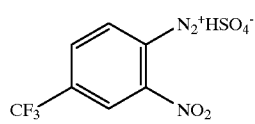

which then couples with a phenol of formula IVa (IVa)

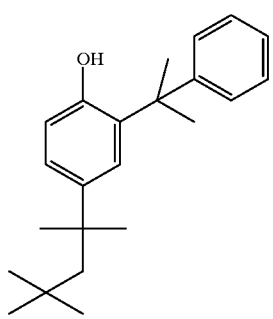

to form the corresponding monoazobenzene compound of formula Vb (Vb)

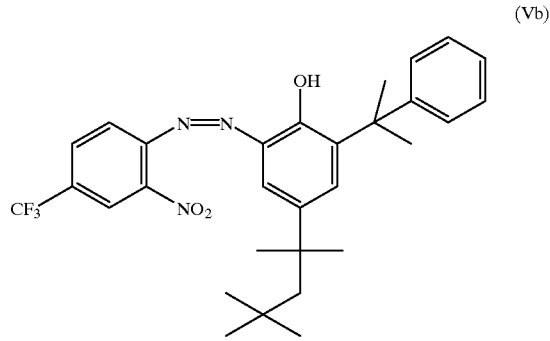

reducing the monoazobenzene intermediate of formula Vb to the corresponding 2H-benzotriazole compound of formula Ib by conventional reduction means.

11. A process according to claim 1 for the preparation of a compound of formula Ic which comprises (Ic)

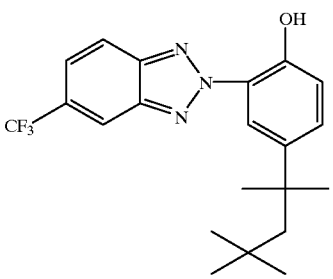

diazotizing a substituted o-nitroaniline compound of formula IIa (IIa)

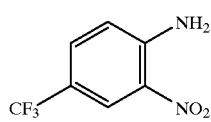

using nitrosylsulfuric acid to form the diazonium salt of formula IIIa (IIIa)

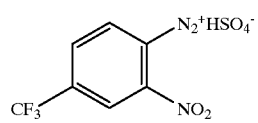

which then couples with a phenol of formula IVa (IVc)

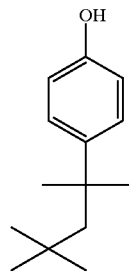

to form the corresponding monoazobenzene compound of formula Vc

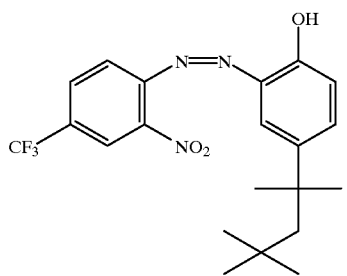

(Vc)

reducing the monoazobenzene intermediate of formula Vc to the corresponding 2H-benzotriazole compound of formula Ic by conventional reduction means.

12. A process according to claim 1 where in the process for making the diazonium salts using a perfluoroalkyl substituted o-nitroaniline (i.e. 4-trifluoromethyl-2-nitroaniline, $CF_3$—ONA), sulfuric acid and an aqueous alkali metal nitrite solution,
   a. the molar ratio of $CF_3$—ONA:sulfuric acid is 1:10 to 1:1;
   b. the molar ratio of $CF_3$—ONA:sodium nitrite is 1:1 to 1:4; and
   c. the temperature used for this reaction is from −30° C. to 50° C.

13. A process according to claim 12 wherein
   a. the molar ratio of $CF_3$—ONA:sulfuric acid is 1:5 to 1:1;
   b. the molar ratio of $CF_3$—ONA:sodium nitrite is 1:1 to 1:2; and
   c. the temperature used for this reaction is from −20° C. to 20° C.

14. A process according to claim 13 wherein
   a. the molar ratio of $CF_3$—ONA:sulfuric acid is 1:2–3.5;
   b. the molar ratio of $CF_3$—ONA:sodium nitrite is 1:1; and
   c. the temperature used for this reaction is from −10° C. to 5° C.

15. A process according to claim 1 where in the process for making the diazonium salts using a perfluoroalkyl substituted o-nitroaniline (i.e. 4-trifluoromethyl-2-nitroaniline, $CF_3$—ONA) and nitrosylsulfuric acid,
   a. the molar ratio of $CF_3$—ONA:nitrosylsulfuric acid is 1:1 to 1:2;
   b. the molar ratio of $CF_3$—ONA:sulfuric acid is 1:1 to 1:10, and
   c. the temperature used for this reaction is from −30° C. to 50° C.

16. A process according to claim 15 wherein
   a. the molar ratio of $CF_3$—ONA:nitrosylsulfuric acid is 1:1 to 1:1.2;
   b. the molar ratio of $CF_3$—ONA:sulfuric acid is 1:2 to 1:7; and
   c. the temperature used for this reaction is from −20° C. to 40° C.

17. A process according to claim 16 wherein
   a. the molar ratio of $CF_3$—ONA:nitrosylsulfuric acid is 1:1;
   b. the molar ratio of $CF_3$—ONA:sulfuric acid is 1:2 to 1:5. ; and
   c. the temperature used for this reaction is from 0° C. to 25° C.

18. A process according to claim 1 wherein the monoazobenzene intermediate of formula V is prepared in a solvent containing a surface active modifier at a temperature of −30° C. to 75° C.

19. A process according to claim 18 wherein the temperature is −20° C. to 50° C.

20. A process according to claim 19 wherein the temperature is −10° C. to 35° C.

21. A process according to claim 18 wherein the solvent is water, an aromatic hydrocarbon, an aliphatic hydrocarbon or a mixture thereof.

22. A process according to claim 21 wherein the solvent is water, toluene, o-xylene, m-xylene, p-xylene, a mixture of said xylenes, mesitylene, pseudocumene, hexane, heptane, octane, nonane or a mixture thereof.

23. A process according to claim 22 wherein the solvent is water, toluene, o-xylene, m-xylene, p-xylene, a mixture of said xylenes, heptane or a mixture thereof.

24. A process according to claim 18 wherein the surface active modifier is selected from the group consisting of emulsifying agents, surfactants, phase transfer agents and dispersants.

25. A process according to claim 24 wherein the surface active modifier is HOSTAPUR® SAS93 (Hoechst) or PETROSUL® M-60 (Penreco).

26. A process according to claim 1 wherein the molar ratio of diazonium salt:phenol is 2:1 to 1:2.

27. A process according to claim 26 wherein the molar ratio of diazonium salt:phenol is 1.5:1 to 1:1.5.

28. A process according to claim 27 wherein the molar ratio of diazonium salt:phenol is 1:1.

* * * * *